United States Patent [19]  [11] 4,076,019
Sain  [45] Feb. 28, 1978

[54] ORTHOPEDIC CAST CONSTRUCTION

[76] Inventor: Bernard S. Sain, 811 Threadneedle Lane No. 285, Houston, Tex. 77079

[21] Appl. No.: 714,701

[22] Filed: Aug. 16, 1976

[51] Int. Cl.² .............................................. A61F 5/04
[52] U.S. Cl. ...................................... 128/83; 128/90; 128/91 R; 427/2
[58] Field of Search ............................ 128/83, 90, 91; 252/194; 428/282; 28/73; 427/2

[56] References Cited

U.S. PATENT DOCUMENTS

| 2,875,752 | 3/1959 | Lovich | 128/83 |
| 3,040,740 | 6/1962 | Parker | 128/83 |
| 3,607,777 | 9/1971 | Winyall | 252/194 X |
| 3,955,565 | 5/1976 | Johnson, Jr. | 128/89 R |

Primary Examiner—Benjamin R. Padgett
Assistant Examiner—E. Suzanne Parr

[57] ABSTRACT

An improved orthopedic cast construction is disclosed. It is intended for application to broken bones, sprains, etc. The improved construction utilizes an elastic sleeve for those instances where the cast is placed on a limb, a second layer of spooled felting material which serves as a buffer against the elastic sleeve, and a third layer formed of a plaster bandage which is applied in multiple wraps soaked in water for the purpose of hardening into a supportive cast. The improvement comprises a felted layer of polyester or cotton fibers with ground silica-gel to adsorb perspiration from the body to keep the cast dry after installation and draws water out of the plaster media to enhance its drying. This protects and extends the life of the cast. It improves comfort to the patient.

9 Claims, No Drawings

ORTHOPEDIC CAST CONSTRUCTION

BACKGROUND OF THE INVENTION

In orthopedic work, broken bones, sprains and other injuries often must be immobilized to obtain suitable healing. Immobilization is ordinarily achieved through the application of a cast on the patient. Two kinds of casts will be described and they differ only in the location on the body of the patient. The first kind is the typical cast installed for a broken limb. Such a cast is constructed in situ placing a type of elastic sleeve on the body of the patient. If, for instance the forearm is broken, the elastic sleeve will typically extend from near the hand up toward the elbow and past as necessary. The elastic sleeve is the material immediately adjacent to the skin and of course, it is placed there to serve as a base for the cast. The cast itself is then shaped around the elastic sleeve which becomes an integral part thereof.

Heretofore, the second layer formed has been several wraps, typically in the range of two to six wraps, of a felted cloth. The soft felting material serves as a cushion and is nonrigid to thereby define a soft media with some give. Multiple wraps of the soft material are placed around the area to be enclosed in the cast. The third material which comprises the cast is a type of plaster bandage. It is a supplied in a continuous spool to be wrapped around the cast area. It is first dipped in water and the water reacts with the plaster bandage to form what is eventually a bandage reinforced plaster cast. Of course, the cast must cure in the typical cure time is in the range of 48 to 72 hours after application. The cure time depends on the number of wraps of the plaster bandage. Representative materials for the fabrication of the cast are supplied by Johnson and Johnson and the three materials are sold under the following respective trademarks:

Stockinette, Sof-rol, and Specialist.

Another type of cast is what might be termed a body cast which might be placed on a person with a broken pelvis, hip, spine or the like. A body cast will have parts corresponding to the three basic constituents named above although they may be supplied in different forms.

Innumerable problems have arisen with plaster casts. First of all, there is the lengthy cure interval. While some breaks are quite painful and significantly incapacitate the patient, often a break will not be so painful and the patient becomes quickly restless during the cure period. This is a particularly difficult problem with small children. They want to get up and move around before the cast has become hard. If they do move around, they may in fact distort or mishape the cast during movement and by so doing reduce the amount of support which the cast furnishes to the break or sprain.

Even though the cast may in fact be cured without distortion during the curing process, they are often subsequently damaged. For instance, they are susceptible to absorbtion of water from either perspiration, humid environments, or other sources. When water impinges on a cast from any of the sources mentioned above, it is absorbed into the plaster cast and weakens the cast. The cast will be weakened, for instance, if the cast is placed on the leg of a patient who subsequently walks in the rain or at a time when there is dew on the ground. The patient may in fact perspire quite freely inside the cast or in attempting to bath, splash a substantial amount of water on the cast. In either case, the water weakens the cast which increases the chance of breakage or distortion after which the cast does not lend the required support to the patient. This manifests itself in poorly set bones or when observed in timely fashion, often requires replacement with a substitute cast.

It is with these problems in mind that the present invention has been devised. It is an apparatus and method which is adapted to be incorporated in a cast. It dries the interior of the cast and particularly that portion of the cast adjacent to the skin. This protects the skin of the patient and moreover, strengthens the cast itself. It enables the cast to dry or cure, thereby achieving a rigid structure and it further keeps it dry and therefore rigid. This particularly is advantageous in casts exposed to substantial amounts of water such as a walking cast placed on the foot and lower leg. It improves the strength of the cast also.

SUMMARY OF THE DISCLOSURE

The preferred embodiment of the present invention is a felted material made of artificial or natural fibers in a felted pad. It is incorporated in a cast at the time of construction of the interior of the plaster bandages which form the cast body itself. The improvement of the present invention is a felted material which is impregnated with a water adsorbing material which holds the water. The best adsorbing material is silica-gel although other materials such as alumina can be used. In any case, the material is finely granulated to pass through a sieve with a screen size of up to about 200. The granulated, water adsorbing material is placed in the fibrous material.

The impregnated felted material is then applied in a cast at the time of fabrication of the cast on the body of the patient. It provides rapid benefit at the time of cast making because it accelerates drying. In addition, it accelerates drying should the cast be substantially damaged by water from multiple sources such as perspiration, rain fall, bathing and the like. It extends the life of the cast substantially. Approximately six times the weight of drying material in water can be absorbed by the present apparatus.

DESCRIPTION OF THE PREFERRED EMBODIMENT

The embodiment of the present invention comprises a felted material made of fibers. The preferable fibers are polyester or cotton fibers. These find dominance in the industry today; other fibers, both man made and natural, can be used but it is believed that the most common and practical fibers are those mentioned above. The fibers are formed into a nonwoven or felted pad. This pad heretofore has been sold under various trademarks, one source being the Johnson and Johnson company which has sold it in widths of two, three, four and six inches under the trademark Sof-rol. It is a definitive strip of material having a specified width and length. The felted material is normally sold in spools although it can be supplied in sheet form also. The precise thickness is subject to variation but it can be in the range of about 1/16th of an inch to about 3/16 inch. Again, these are scale factors which can be varied, the intention being the furnishing of a felted material which serves as a pad in the fabrication of a cast.

The improvement of the present invention contemplates impregnation of the felted material with silica-gel, alumina or other suitable moisture adsorbants. It is preferably granulated to a screen size of about 200 mesh. At this screen size, it provides an adsorbant surface area upwards of 1000 square meters per gram of material. This material is placed in the felted cloth. It is sifted or otherwise placed in the interstical openings of the nonwoven pad. The manner of binding the granulated material is subject to variation; it is sufficient merely to note that granulated material can be impregnated into a woven material and it will hold its position indefinitely. If there is a tendency for it to sprinkle out in the form of a powder, the nonwoven fabric can be encased on both sides with an external coating. One type of external coating is a fine mesh gauze or cheese cloth. Another suitable manner of binding the granulated water adsorbent material in the nonwoven fabric is to use a nonsoluable starch material.

The cast material of the present invention is suitably fitted for fabrication of a cast. The cast is formed in the manner described in the beginning of this disclosure. That is to say, the nonwoven fabric of the present disclosure constitutes the intermediate layer of the assembled cast. As the intermediate layer, it is exposed to the skin of the patient and hence is able to adsorb perspiration through the porous stocking, one version being the Stockinette. It is also able to adsorb water which runs under the cast along the skin of the patient as might occur at the time of bathing the patient. In addition, it is exposed to the plaster bandages. It accelerates drying of the plaster bandages which are used to form the body of the cast. As the material dries, any water which is in the plaster bandages is adsorbed into the silica-gel. As the cast dries, its strength increases. Because the present invention accelerates curing, the cast becomes strong much sooner and is able to be used much sooner. As for example in the fabrication of a walking cast, the patient is able to walk much sooner. Moreover, when it cures, the strength reaches an acceptable level much sooner. This avoids flaking of the cast. This also avoids damage such as breakage whereby a replacement cast has to be put on the patient before the break or sprain has healed.

The present invention further includes a method of rapidly curing a cast including the use of plaster bandages which are wetted by a mixture of water and ordinary rubbing alcohol. Other types of alcohol can be used but they are more expensive. For instance, so-called "wood" alcohol is less expensive because it is not subject to alcohol taxes normally levied on alcohol beverages. The optimum solution is in the range of about half water and half alcohol, and in particular the nondrinkable form of alcohol. Alcohol appears to evaporate more rapidly than water to thereby decrease the curing time. Thus, the use of a mixture of about half water and half alcohol in conjunction with the silica-gel impregnated nonwoven cloth of the present invention materially speeds curing of the cast.

At the time of application, the plaster bandages are dipped or otherwise submerged in a mixture of water and alcohol. The bandages are then wrapped around the silica-gel impregnated pad which is itself formed by multiple wraps of the nonwoven material disclosed herein. This then defines a cast which is formed by the orthopedic surgeon on the body of the patient which cures much more rapidly by virtue of the water adsorption into the silica-gel in the interior of the cast and more rapid surface evaporation of the water-alcohol mixture. The speed with which the plaster bandages dry is dependent on many variables including the humidity of the air in the near vicinity, the surface area exposed on the cast, the room temperature and so on. It is sufficient to note that under most circumstances that the use of the silica-gel impregnated padding material disclosed herein and the use of a solvent of water-alcohol mixture as taught herein measurably accelerates the time required to place a cast on a patient and cure it to the point where it cans stand the intended wear and tear that the cast will be exposed to.

Many alterations and variations in the disclosed method and apparatus may be incorporated. For example, the shape and form of the nonwoven or felted material disclosed herein is subject to variation. It can be made in sheet or strip form for ease of manufacture and storage. It normally is applied in multiple wraps, often between two and six layers are built up around the limb or body to be cast. In addition, the cast material can be something other than plaster bandages. Older techniques are sometimes used in the application of the plaster around the exterior of the multiple layer cast. For example, gauze and other bandages can be placed around the cast and the cast can be completed on the exterior by placing plaster on the exterior. However, the ideal material is plaster bandages which enable the orthopedic surgeon to form a cast in fairly rapid order.

The granulation of the water adsorbing material is subject to variation. One measure is 200 mesh size although smaller or larger particles can be used. Larger particles have reduced surface area; smaller particles become so small that they tend to form dust which is an irritant prior to wetting of the bandages.

The foregoing is directed to the preferred embodiment but the scope thereof is determined by the claims which follow.

I claim:

1. For use in a built up cast in orthopedic surgical work, a felted fibrous material having impregnated therein a water adsorbing agent of silica-gel or alumina which material is to be placed on the interior of a plastic cast.

2. The felted fibrous material of claim 1 wherein said fibrous material is formed into a pad of specified thickness and includes said adsorbing agent as a granulated material in the interstical openings therein.

3. The felted fibrous material of claim 1 wherein said adsorbing agent is ground to a fineness as small as 200 mesh.

4. The felted fibrous material of claim 1 wherein said fibrous material includes a cotton fiber pad impregnated with silica-gel.

5. A method of forming a cast on a patient comprising the step of placing moistened plaster bandages on a patient to form a cast, which cures on the patient after the passage of time, and including the step of positioning on the interior of said cast a fibrous material having impregnated therein a water adsorbing agent of silica-gel or alumina prior to curing of the cast.

6. The method of claim 5 including the step of forming a fibrous layer of multiple wraps beneath the cast prior to curing which fibrous layer includes the water adsorbing material impregnated therein.

7. The method of claim 6 wherein the "fibrous" layer is formed at a location to be exposed to perspiration of the patient.

8. The method of claim 5 including the step of initially wetting the plaster bandages with a water and alcohol solution prior to placing them on a patient.

9. The method of claim 8 wherein the water and alcohol are mixed about half and half.

* * * * *